United States Patent [19]

Takahashi et al.

[11] Patent Number: 4,778,374

[45] Date of Patent: Oct. 18, 1988

[54] APPARATUS FOR FORMING TAMPON INSERTER TIP

[75] Inventors: Hiroshi Takahashi, Machida; Yasutami Muto, Koshigaya; Toru Okino, Hatano, all of Japan

[73] Assignee: Lion Corporation, Tokyo, Japan

[21] Appl. No.: 126,727

[22] Filed: Nov. 30, 1987

[51] Int. Cl.$^4$ .............................................. B29C 57/10
[52] U.S. Cl. .................................... 425/343; 425/392; 604/16
[58] Field of Search ............... 425/340, 341, 343, 392, 425/393, 453, 454; 264/296; 269/229; 604/14, 16, 904

[56] References Cited

U.S. PATENT DOCUMENTS

| | | | |
|---|---|---|---|
| 647,993 | 4/1900 | Schmidt | 264/296 X |
| 3,433,225 | 3/1969 | Voss et al. | 604/14 |
| 3,581,744 | 6/1971 | Voss et al. | 604/14 |
| 3,694,859 | 10/1972 | Glasman | 425/340 |
| 3,895,634 | 7/1975 | Berger et al. | 604/14 |
| 4,104,013 | 8/1978 | Kelly et al. | 425/340 X |
| 4,276,881 | 7/1981 | Liladnitkul et al. | 604/16 X |
| 4,291,696 | 9/1981 | Ring | 604/904 X |
| 4,302,174 | 11/1981 | Hinzmann | 425/392 X |

FOREIGN PATENT DOCUMENTS

| | | | |
|---|---|---|---|
| 166149 | 12/1950 | Japan | 425/343 |
| 36553 | 3/1983 | Japan | 425/392 |

Primary Examiner—Richard L. Chiesa
Attorney, Agent, or Firm—Oblon, Fisher, Spivak, McClelland & Maier

[57] ABSTRACT

An apparatus for continuously and rapidly forming petal-like segments at the tip of a tampon inserter into a hemispherically curved shape. Sets of molds are mounted on a support table on a rotary table turned about a shaft. Each set comprises a heating mold to heat and soften the tip of the tampon inserter and a cooling mold to shape while being cooled the heated and softened tip. The heating and cooling molds are moved by a cam so that either of the two molds is placed above the tampon inserter held in position by a gripper. The gripper comprises a pair of gripper segments that are opened and closed by a cam on the shaft and raised and lowered by another cam on the same shaft. The cams are adapted to release the tampon inserter from the gripper after the tampon inserter has been put first in the heating mold and then in the cooling mold. The tip of the tampon inserter held by the gripper first enters the heating mold to get heated. While the heated tip descends temporarily, the cooling mold is brought to above the tampon inserter. As the tampon inserter rises again, its tip comes in contact with the inner surface of the cooling mold, in which the tip is formed into a hemispherically curved shape while being cooled.

5 Claims, 4 Drawing Sheets

APPARATUS FOR FORMING TAMPON INSERTER TIP

FIELD OF THE INVENTION

This invention relates to an apparatus for forming the petal-like segments at the tip of the outer cylinder of a double-cylinder sanitary tampon inserter of synthetic resin into a hemispherically curved shape.

DESCRIPTION OF THE PRIOR ARTS

A double-cylinder sanitary tampon inserter of the type disclosed, for example, in U.S. Pat Nos. 4,291,696 and 4,276,881 comprises an inner cylinder doubling as a tampon holder and a push rod and an outer cylinder to hold the inner cylinder. The claws provided on the outer cylinder are allowed to project into the inner cylinder through the grooves cut in the inner cylinder so that the claws keep a tampon inside the outer cylinder when the inner cylinder is withdrawn. This type of tampon inserter has the advantage of greater compactness and portability over other types of conventional tampon inserters.

With this type of sanitary tampon inserter of synthetic resin, the tip of the outer cylinder is formed into hemispherically curved petal-like segments. Because of the limitations involved in the shape of molds and the number of shots in injection molding, it is advantageous to form straight petal-like segments first and then curve such straight segments into the desired hemispherical shape in a subsequent process, rather than forming curved segments in the beginning. This type of molding method is already known, as is proposed in U.S. Pat. No. 3,895,634, Japanese Provisional Patent Publication Nos. 55-166149 and 58-36553.

The method disclosed in the specification of JP A No. 58-36553 which has advantages for industrial use divides the tip of the outer cylinder into straight petal-like segments which are first put into a heating mold having a hemispherically curved recess and then, after being heated and softened, into a cooling mold having a similar hemispherically curved recess for hardening.

Heretofore, however, no appropriate method nor apparatus has been proposed for continuously and rapidly accomplishing such tampon inserter forming operation.

SUMMARY OF THE INVENTION

An object of this invention is to provide a practical apparatus for continuously and rapidly accomplishing the aforementioned operation to form the petal-like segments at the tip of a tampon inserter into a hemispherically curved shape.

Another object of this invention is to provide an apparatus for fully automatically and efficiently forming the petal-like segments at the tip of a tampon inserter into a hemispherically curved shape.

In order to achieve the above objects, a tampon inserter tip forming apparatus according to this invention has a rotary table that is turned about a shaft by a drive unit, with sets of molds, each of which comprises a heating mold in which the tip of the tampon inserter is heated and softened and a cooling mold in which the heated and softened tip is shaped while being cooled, disposed around the periphery of the rotary table. A cam mechanism is provided on the shaft so that either of the heating and cooling molds is positioned, at one or the other end of a guide, above a tampon inserter held by a gripper. One tampon inserter gripper is provided for each mold unit on the rotary table. The tampon inserter gripper comprises a pair of gripper segments that are opened and closed by another cam mechanism and raised and lowered by still another cam mechanism provided on the shaft. The cam mechanisms are so arranged that the gripper releases the tampon inserter which has been put first in the heating mold and then in the cooling mold.

When the drive unit turns the rotary table of this forming apparatus, each of the cam mechanisms interlockingly moves the heating and cooling molds, opens and closes the gripper, and raises and lowers the gripper. Accordingly, the tip of a tampon inserter held by the gripper first enters the heating mold. While the heated tip is lowered temporarily, the cooling mold is moved to above the tampon inserter. When the tampon inserter is raised again, the heated tip comes in contact with the inner surface of the cooling mold to become hemispherically shaped while being cooled. As such, this invention provides a practical automatic forming apparatus that continuously and rapidly forms the petal-like segments at the tip of a tampon inserter into a hemispherically curved shape.

DESCRIPTION OF THE PREFERRED EMBODIMENT

Now a preferred embodiment of this invention will be described in detail by making reference to the accompanying drawings.

FIGS. 1 to 5 illustrate an apparatus for forming the tip of a tampon inserter embodying the principle of this invention. A shaft 2 to support the whole apparatus is erected at the center of a base 1, with a rotary table 3 rotatably mounted on the shaft 2. A drive unit, not shown, turns the rotary table 3 through a drive wheel 4. While the rotary table 3 is thus turned around the shaft 2 once, the tip of a tampon inserter is formed as elaborated below.

The rotary table 3 carries two support tables 5 and 6, the former placed above the latter. While the upper support table 5 carries a set of molds 7 and 8 for forming the tip of a tampon inserter A, the lower support table 6 carries a mechanism to hold and transfer the tampon inserter A to where the molds 7 and 8 are positioned.

Figure 1:
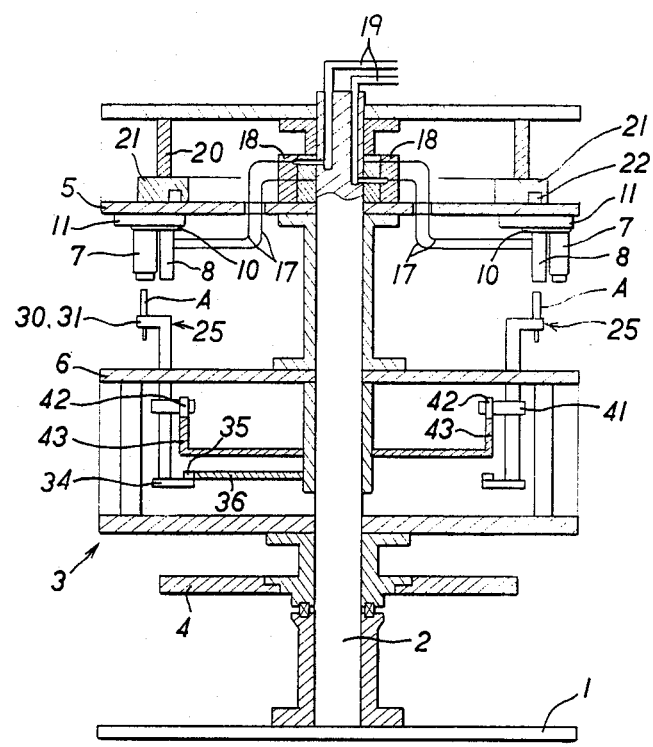
FIG. 1 is a general cross-sectional view of a forming apparatus according to this invention.
Figure 2:
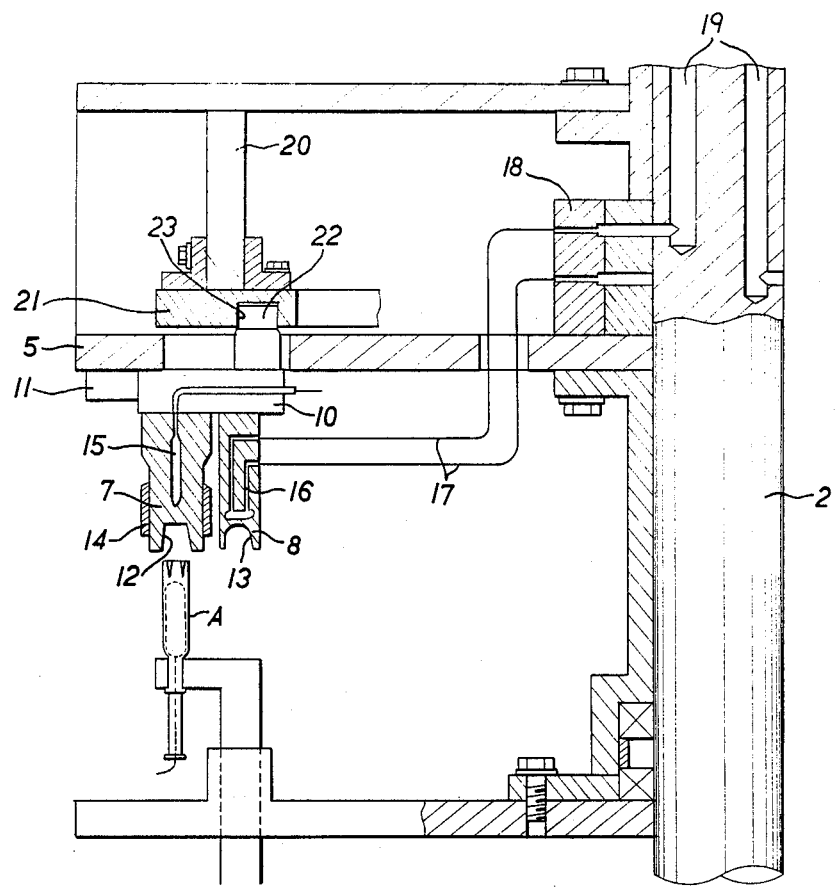
FIGS. 2 and 3 are a vertical cross-sectional view and a bottom view showing the principal parts of molds carried by a rotary table and other mechanisms associated therewith.
Figure 3:
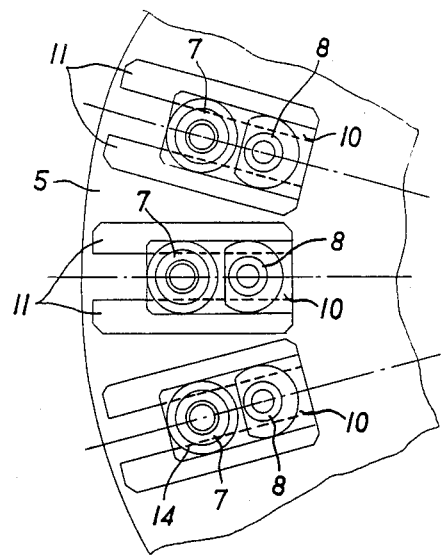

Each pair of the molds 7 and 8 carried by the upper support table 5 consists of a heating mold 7 for heating and softening the tip of the tampon inserter A and a cooling mold 8 for cooling the heated and softened tip, as shown in FIGS. 1 to 3. The paired heating and cooling molds 7 and 8 are attached to a slider 10 with a given space left therebetween. The slider 10 is slidably supported between a pair of guides 11 attached to the support table 5. With the slider 10 supported by the guides 11 as illustrated, the cavities 12 and 13 provided in the heating and cooling molds 7 and 8 open downward. When the slider 10 travels to one or the other end of the guides 11, either of the cavities 12 and 13 comes into the position above the tampon inserter A held by a gripper 25 to be described later. Namely, the center-to-center distance between the cavities 12 and 13 is equal to the stroke of the slider 10.

Pairs of the guides 11 are radially attached to the support table 5 around the shaft 2, with each pair of the guides 11 supporting the slider 10 to which the molds 7 and 8 are attached.

The heating mold 7 has a band heater 14 wound therearound and a temperature sensor 15 mounted therein, the heater 14 and the sensor 15 being connected to a controller, not shown, so that the temperature in the cavity 12 is kept substantially constant. The cooling mold 8 has an inner passage 16 through which cooling water is passed. The water passage 16 communicates with water supplying and draining passages 19 in the shaft 2 through a flexible tube 17 and a manifold 18. Water supplied and drained through the passages 19 cools the inside of the cavity 13.

The slider 10 slidably supported by the guides 11 has a cam follower 22 projecting upward through a slot in the support table 5. The cam follower 22 is adapted to move along a ring-shaped cam 21 attached to a support frame 20 fastened to the shaft 2. While the cam follower 22 consists of a roller rotatably supported by the slider 10, the ring-shaped cam 21 consists of an annular plate cut with a cam groove 21 and mounted around the shaft 2.

In the heating area around the shaft 2, in which the tampon inserter A is heated, the cam groove 23 allows the slider 10 to slide to one end of the guides 11, thereby bringing the heating mold 7 into the position above the tampon inserter A. In the cooling area around the shaft 2, in which the tampon inserter A is cooled, the cam groove 23 allows the slider 10 to slide to the other end of the guides 11, thereby bringing the cooling mold 8 into the position above the tampon inserter A.

Meanwhile, the mechanism for holding and transferring the tampon inserter A consists of a gripper 25 that grips and brings a successively fed tampon inserter A into the desired position below the molds 7 and 8. As many grippers 25 as the pairs of the molds 7 and 8 are mounted on the support table 6.

Figure 5:
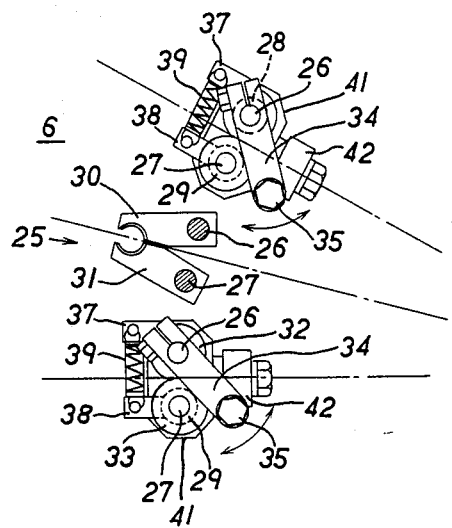
FIGS. 4 and 5 are a vertical cross-sectional view and a bottom view showing the principal parts of a mechanism to hold and transfer a tampon inserter.
Figure 4:
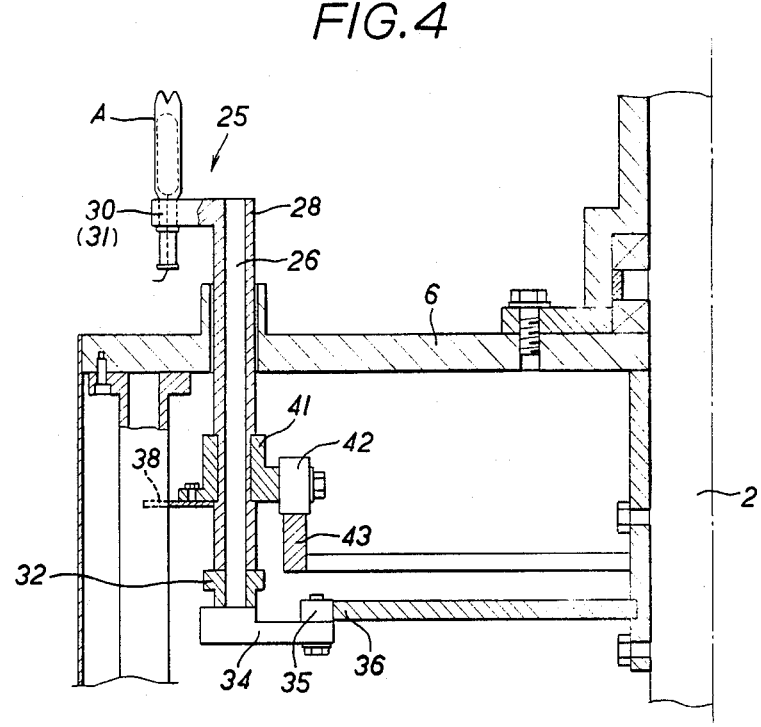

The gripper 25 comprises sleeves 28 and 29 that are fitted over a pair of gripper shafts 26 and 27 in such a manner as not to rotate but to slide with respect to each other by means of spline or other engaging means, as elaborated in FIGS. 4 and 5. The sleeves 28 and 29 are slidably passed through the support table 6, with a pair of gripper segments 30 and 31 to pinch the tampon inserter A attached to the tip of the sleeves 28 and 29. Mating spur gears 32 and 33 are attached to the lower portion of the gripper shafts 26 and 27. A lever 34 is attached to the lower end of the gripper shaft 26. A cam follower 35 rotatably attached to the tip of the lever 34 is kept in contact with a sector cam 36 that is fastened to the shaft 2 to open and close the gripper. A spring 39 to urge the gripper segments 30 and 31 in the closing direction is provided between projections 37 and 38 protruding from the gripper shafts 26 and 27.

When the sector cam 36 presses the cam follower 35 and the lever 34 turns clockwise in FIG. 5 at the point where a tampon inserter A is delivered, the mating spur gears 32 and 33 turn the gripper shafts 26 and 27 in opposite directions to open the gripper segments 30 and 31 against the force of the spring 39. When the segment cam 36 ceases to press, thereby returning the lever 34 to the original position, the grippers 30 and 31 close.

A support 41 is fitted over each of the sleeves 28 and 29 in such a manner that the sleeves 28 and 29 are rotatable therein but are allowed to move integrally therewith in the axial direction. The support 41 rotatably supports a cam follower 42 that is kept in contact with a lifting cam 43 fastened to the shaft 2. The lifting cam raises and lowers the gripper 25 by means of the surface irregularities on the cam face contacting the cam follower 42, thereby moving the tampon inserter A into and away from the cavities 12 and 13 in the molds 7 and 8.

While the drive unit turns the rotary table 3 in the tampon inserter tip forming apparatus described above, the ring-shaped cam 21 moving the slider 10 that supports the molds 7 and 8, the sector cam 36 opening and closing the gripper 25 and the lifting cam 43 raising and lowering the gripper 25 move the cam followers 22, 35 and 42, respectively, to accomplish the forming of the tip of the tampon inserter A.

In the introductory area where a separate transfer means brings a tampon inserter A onto the rotary table 3, the cam 21 brings the heating mold 7 to above the tampon inserter A, with the gripper 25 kept in the lowered position by the lifting cam 43 and kept open by the cam follower 35 that is pressed by the sector cam 36. When the tampon inserter A is sent into the gripping position of the gripper 25, the sector cam 36 releases the cam follower 35, whereupon the gripper 25 closes to hold the tampon inserter A.

As the rotary table 3 turns, the lifting cam 43 raises the gripper 25 holding the tampon inserter A until the tip thereof enters the heating mold 7 where heating is done. On completion of heating, the lifting cam 43 temporarily lowers the gripper 25. While the gripper 25 is thus held in the lowered position, the cam 21 moves the cooling mold 8 to above the tampon inserter A. When the lifting cam 43 raises the tampon inserter A again, the heated tip thereof comes in contact with the inner surface of the cooling mold 8 and gets thereby formed into a hemispherically curved shape while being cooled.

When the tip is cooled and formed, the lifting cam 43 lowers the gripper 25, which, in turn, releases the tampon inserter A when the sector cam 36 presses the cam follower 35 and gets ready for the acceptance of the next tampon inserter A.

With the preferred embodiment just described, the upper support table 5 carries the set of forming molds 7 and 8 while the lower support table 6 carries the means to hold and transfer a tampon inserter A. But a reversed arrangement is possible, as well.

What is claimed is:

1. An apparatus for forming the tip of a tampon inserter which comprises a rotary table turned about a shaft by a drive unit, sets of molds provided around the periphery of a support table on the rotary table, each set comprising a heating mold for heating and softening the tip of a tampon inserter and a cooling mold for shaping while being cooled the heated and softened tip of the tampon inserter, the heating and cooling molds being adapted to be moved by a cam to one or the other end of guides so that either of the heating and cooling molds is placed above the tampon inserter held in position, grippers to hold tampon inserters in position provided on another support table on the rotary table, each gripper being adapted to work in conjunction with each set of the heating and cooling molds and comprising a pair of gripper segments adapted to be opened and closed by another cam and raised and lowered by still another cam, said cams being mounted on the shaft and adapted to release the tampon inserter after the tampon inserter has been put first in the heating mold and then in the cooling mold.

2. An apparatus for forming the tip of a tampon inserter according to claim 1, in which the heating and cooling molds are mounted on a slider with a space left therebetween, the slider being slidably supported by a pair of guides provided on the support table, and a cam follower projecting from the slider is adapted to be movable along a ring-shaped cam fastened to the shaft.

3. An apparatus for forming the tip of a tampon inserter according to claim 1, in which the gripper to hold a tampon inserter in position comprises a pair of gripper segments to pinch a tampon inserter therebetween, the gripper segments being attached to the tip of sleeves fitted over a pair of gripper shafts in such a manner as not to rotate but to slide with respect to each other and adapted to be opened and closed by the rotation of the gripper shafts caused by a cam on the shaft and raised and lowered by the up and down motion of the sleeves caused by another cam on the shaft.

4. An apparatus for forming the tip of a tampon inserter according to claim 3 which comprises mating gears provided at one end of the gripper shafts, a spring to urge the paired gripper segments in the closing direction, a lever attached to one of the gripper shafts, and a cam follower attached to the tip of the lever and kept in contact with a sector cam fastened to the shaft for opening and closing the gripper.

5. An apparatus for forming the tip of a tampon inserter according to claim 3 which comprises a support, the support being fitted to the sleeve carrying the gripper segment so that the sleeve is rotatable therein and adapted to move integrally therewith in the axial direction, and a cam follower attached to the support and adapted to be raised and lowered by a lifting cam fastened to the shaft.

* * * * *